United States Patent
Lin et al.

(10) Patent No.: US 8,585,832 B2
(45) Date of Patent: Nov. 19, 2013

(54) WASHER AND DECONTAMINATOR WITH LID CONTROL

(75) Inventors: Szu-Min Lin, Irvine, CA (US); Robert C. Platt, Laguna Niguel, CA (US); Peter C. Zhu, Cupertino, CA (US)

(73) Assignee: Ethicon, Inc., Somerville, NJ (US)

( * ) Notice: Subject to any disclaimer, the term of this patent is extended or adjusted under 35 U.S.C. 154(b) by 824 days.

(21) Appl. No.: 12/781,891

(22) Filed: May 18, 2010

(65) Prior Publication Data

US 2010/0224224 A1 Sep. 9, 2010

Related U.S. Application Data

(62) Division of application No. 11/694,071, filed on Mar. 30, 2007, now Pat. No. 7,749,330.

(51) Int. Cl.
*B08B 3/04* (2006.01)
*B08B 13/00* (2006.01)

(52) U.S. Cl.
USPC ..... 134/57 R; 134/56 R; 134/58 R; 134/95.1; 134/198; 422/28; 422/292

(58) Field of Classification Search
USPC .................. 134/56 R, 57 R, 58 R, 198, 95.1; 422/292, 28
See application file for complete search history.

(56) References Cited

U.S. PATENT DOCUMENTS

| | | |
|---|---|---|
| 4,783,321 A | 11/1988 | Spence |
| 4,948,566 A | 8/1990 | Gabele et al. |
| 6,209,591 B1 | 4/2001 | Taggart |
| 6,217,835 B1 | 4/2001 | Riley et al. |
| 6,365,102 B1 | 4/2002 | Wu et al. |
| 6,365,103 B1 | 4/2002 | Fournier |
| 6,800,245 B1 | 10/2004 | Erbe et al. |
| 2002/0045328 A1 | 4/2002 | Kobayashi |
| 2002/0098139 A1 | 7/2002 | Sparks |
| 2004/0062692 A1 | 4/2004 | Lin et al. |
| 2004/0105780 A1 | 6/2004 | Lin et al. |
| 2005/0025664 A1* | 2/2005 | Selig et al. ................ 422/28 |
| 2005/0025671 A1* | 2/2005 | Kral et al. ................ 422/62 |
| 2005/0025685 A1* | 2/2005 | Selig et al. ................ 422/292 |
| 2005/0025686 A1 | 2/2005 | Sargent et al. |
| 2005/0042130 A1 | 2/2005 | Lin et al. |
| 2005/0163655 A1 | 7/2005 | Lin et al. |
| 2005/0238530 A1* | 10/2005 | Frieze et al. ................ 422/1 |
| 2007/0207074 A1* | 9/2007 | Jethrow ................ 422/292 |
| 2007/0212278 A1* | 9/2007 | Jethrow et al. ................ 422/292 |
| 2008/0236621 A1 | 10/2008 | Lin et al. |
| 2008/0240979 A1 | 10/2008 | Lin et al. |

* cited by examiner

*Primary Examiner* — Michael Kornakov
*Assistant Examiner* — Benjamin L Osterhout

(57) ABSTRACT

A method and apparatus provide for automatically cleaning and decontaminating medical instruments. The method comprising the steps of: a) placing the medical instruments into a container after their use in a medical procedure; b) closing the container to seal the instruments inside whereby to prevent personnel contact with the instruments and any contaminants which might be thereon; c) inserting the sealed container into a washer/decontaminator and sealing the washer/decontaminator; d) the washer/decontaminator automatically opening the container and applying a washing fluid thereto to wash the instruments within the container; and e) the washer/decontaminator automatically applying a disinfectant to the container to disinfect the instruments whereby to allow safe handling thereof by personnel.

5 Claims, 12 Drawing Sheets

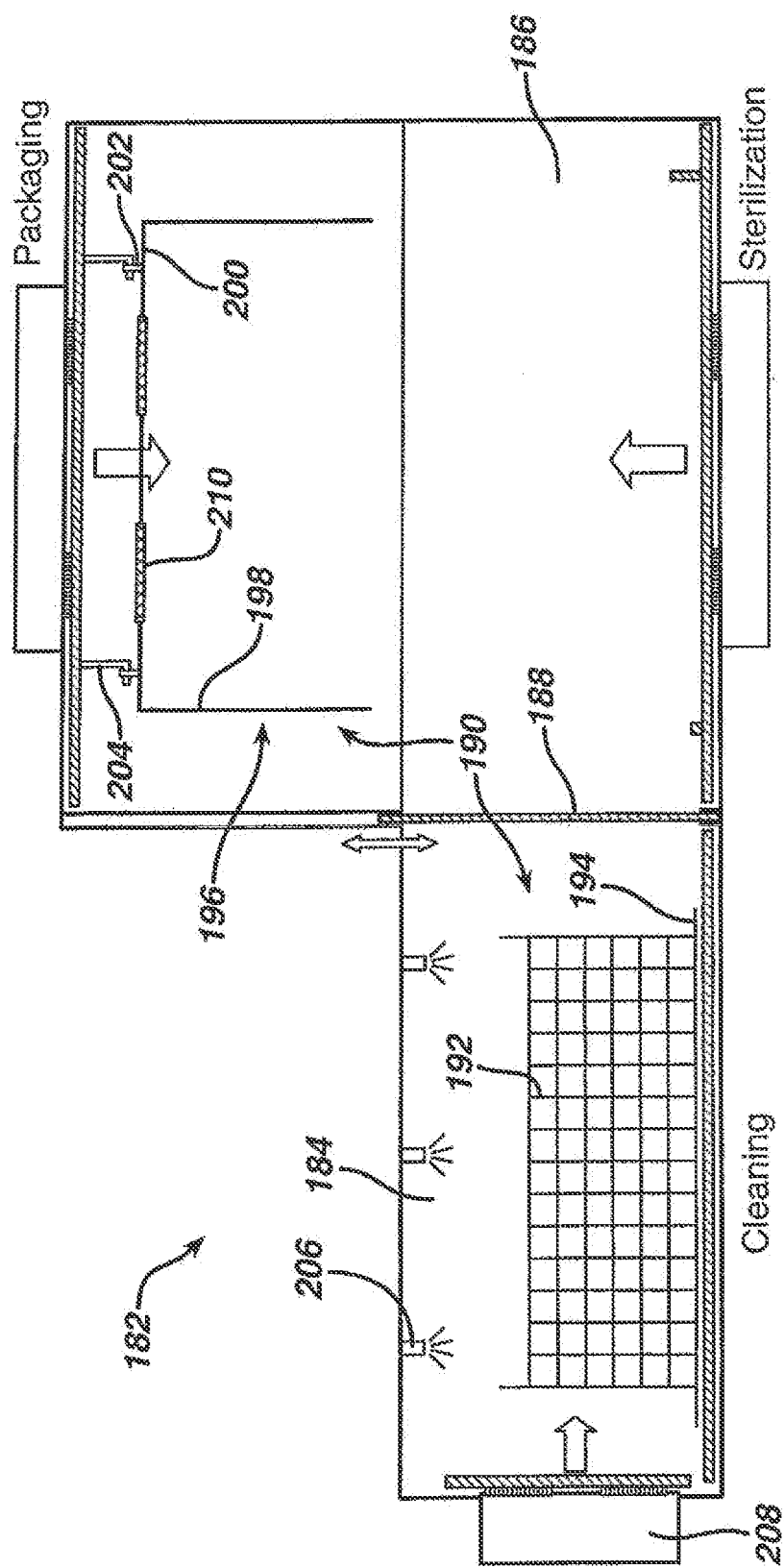

WASHER AND DECONTAMINATOR WITH LID CONTROL

CROSS-REFERENCE TO RELATED APPLICATION

This application is a divisional of U.S. application Ser. No. 11/694,071 filed on Mar. 30, 2007 now U.S. Pat. No. 7,749,330.

BACKGROUND OF THE INVENTION

The present invention relates to the washing and sterilization of medical instruments, and to an apparatus for achieving both washing and sterilization.

After use reusable medical instruments must be both washed and then sterilized before they can be reused. They are placed into a container at the point of use and then transported to the hospital central supply area for further processing. Typically, washing is performed either by hand using a detergent and mechanical scrubbing devices such as brushes, are in a machine which typically directs jets of detergent laid in water at the device to effect cleaning. The devices are contaminated with potentially dangerous pathogens which require the personnel performing such cleaning to wear appropriate protective gear such as gloves, gowns, masks etc.

After the device has been washed it is decontaminated, which typically comprises a brief contact with a decontaminating agent such as bleach or steam sufficient to kill the most dangerous pathogens such as hepatitis. The instruments may then be safely handled for inspection and processed for sterilization. This typically involves each instrument being packaged in a semi-permeable pouch permeable to a sterilizing agent yet impermeable to microorganisms, or by being packaged into a tray which is then wrapped in CSR wrap which is semi-permeable. It is then placed into and processed in a sterilizer such as a steam sterilizer or a hydrogen peroxide gas plasma sterilizer such as the STERRAD Sterilizer available from Advanced Sterilization Products Division Ethicon, Inc., Irvine, Calif. Such a sterilizer is depicted in U.S. Pat. No. 6,365,102, which is hereby incorporated by reference.

The cleaning and decontamination procedure requires special care. The personnel require protective garb when handling the contaminated instruments, and this presents an issue for the hospital as they typically then must provide a special area for such handling and provide additional air conditioning to such area to compensate for the extra garb worn by the personnel. It is desired that personnel be able to effect cleaning and decontamination without having to manually unseal the container bearing contaminated instruments potentially exposing them to dangerous pathogens.

SUMMARY OF THE INVENTION

A method according to the present invention provides for automatically cleaning and decontaminating medical instruments. The method comprising the steps of: a) placing the medical instruments into a container after their use in a medical procedure; b) closing the container to seal the instruments inside whereby to prevent personnel contact with the instruments and any contaminants which might be thereon; c) inserting the sealed container into a washer/decontaminator and sealing the washer/decontaminator; d) the washer/decontaminator automatically opening the container and applying a washing fluid thereto to wash the instruments within the container; and e) the washer/decontaminator automatically applying a disinfectant to the container to disinfect the instruments whereby to allow safe handling thereof by personnel.

Preferably, step e) disinfects the instruments to a sterility assurance level (SAL) of 10-2. In one aspect of the invention the SAL is measured against *b. stearothermophilus*. In a separate aspect of the invention the SAL is measured against hepatitis C. More preferably, step e) disinfects the instruments to a sterility assurance level of 10-3 against *b. stearothermophilus*. Most preferably, step e) disinfects the instruments to a sterility assurance level of 10-4 against *b. stearothermophilus*.

Preferably, the container has a lid and the step of opening the container comprises opening the lid. Preferably, the lid is closed after step e).

Preferably, agitation is applied to the washing fluid during step d), such as by mechanical agitators, by flowing it through nozzles, or via one or more ultrasonic transducers.

In one aspect of the invention, step of opening the container comprises opening both a top and a bottom portion thereof. Preferably, the step of opening the container comprises putting lateral sides of the container into fluid communication with the washing fluid, as for instance when the container comprises a basket having sides with multiple apertures therethrough and the step of opening the container comprises the step of exposing the sides to the washing fluid.

An apparatus provides for cleaning and decontaminating one or more medical instruments sealed within a container. The apparatus comprises a chamber for receiving the container and opening means for opening the container automatically while it is inside the chamber. A washing fluid distribution system connects to the chamber whereby to apply washing fluid to the device within the chamber, and a source of decontamination fluid connects to the chamber whereby to decontaminate the instruments after washing.

Preferably, the opening means comprises one or more arms attached to a lid of the container and a actuator for causing the one or more arms to lift the lid off of the container.

Preferably, the decontamination fluid comprises hydrogen peroxide vapor.

Preferably, a computer control system connects to the opening means, the washing fluid distribution system and the source of decontamination fluid and is programmed to, after the chamber is sealed, open the container via the opening means, wash the device via the washing fluid distribution system and decontaminate the device via the decontamination fluid.

Preferably, the container comprises an internal basket and removable sides and top whereby to expose the basket for efficient washing. It can further comprises a plurality of upwardly extending resilient fingers therein whereby to limit movement of the instruments within the basket.

BRIEF DESCRIPTION OF THE DRAWINGS

FIGS. 2a and 2b are cut-away side elevation views of a chamber according to the present invention receiving the container of FIG. 1a.

FIG. 3 is a block diagram of an integrated sterilization and washing system according to the present invention incorporating the chamber of FIG. 2a.

FIG. 4b is an end elevation view of the container of FIG. 4a.

FIGS. 5a and 5b are cut-away side elevation views of a chamber according to the present invention receiving the container of FIG. 4a.

FIG. 7c is a side elevation view of a chamber for receiving the container of FIG. 7a.

FIG. 8b is a cut away side elevation view of a chamber according to the present invention receiving two of the containers of FIG. 8a.

FIG. 11 is a cut away side elevation view of an integrated washer/sterilizer according to the present invention.

DETAILED DESCRIPTION OF THE INVENTION

Figure 1A:
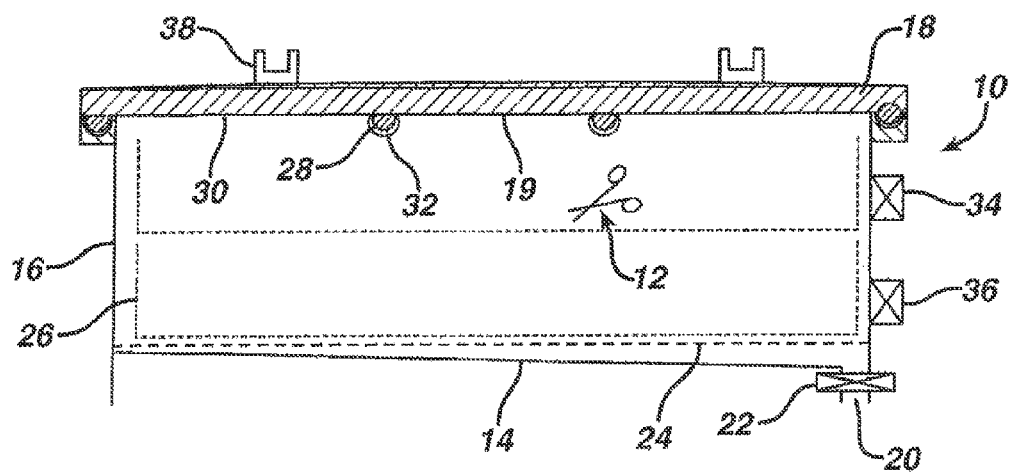
FIGS. 1a and 1b are side elevation views of a container according to the present invention.
Figure 1B:
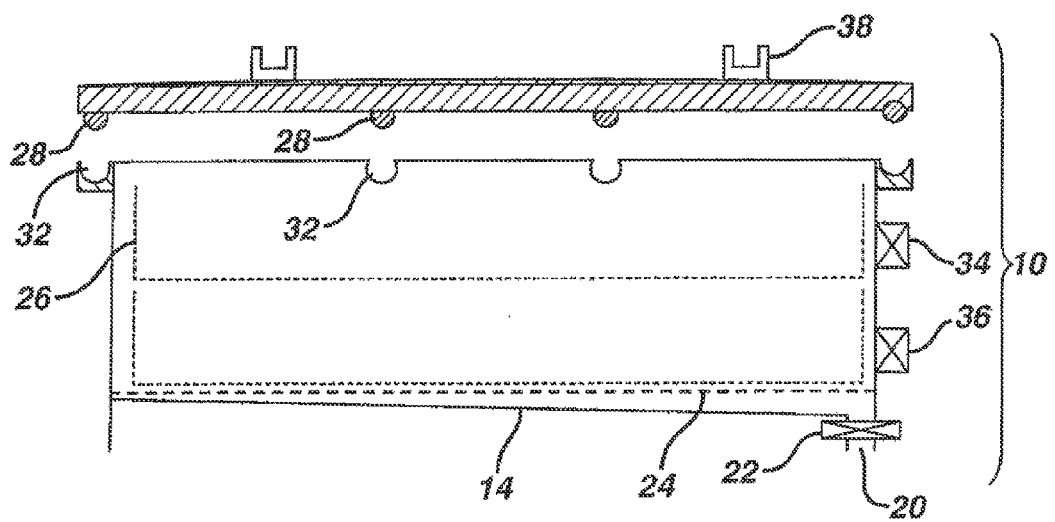

FIGS. 1a and 1b show a container 10 for receiving one or more medical instruments 12. The container comprises a bottom 14 and upstanding sidewalls 16. A lid 18 fits to the top of the sidewalls 16 to seal the container 10. The bottom 14 is sloped and has a drain 20 with a closure valve 22. A grid 24 rests slightly above the bottom 14 and supports one or more instrument receiving baskets 26. Both the grid 24 and baskets 26 are preferably formed from a mesh having large enough holes to freely pass cleaning solution and may be formed of stainless steel, aluminum, polyethylene, polypropylene, or styrene, TEFLON polytetrafluoroethylene and other suitable materials. Several bosses 28 project from a lower surface 30 of the lid 18 and engage with meeting channels 32 in the sidewalls 16 to help position the lid 18 correctly. First and second valved openings 34 and 36 enter the container 10 through one of the sidewalls 16. Also, brackets 38 on the lid 18 are provided for machine grasping.

Figure 2A:
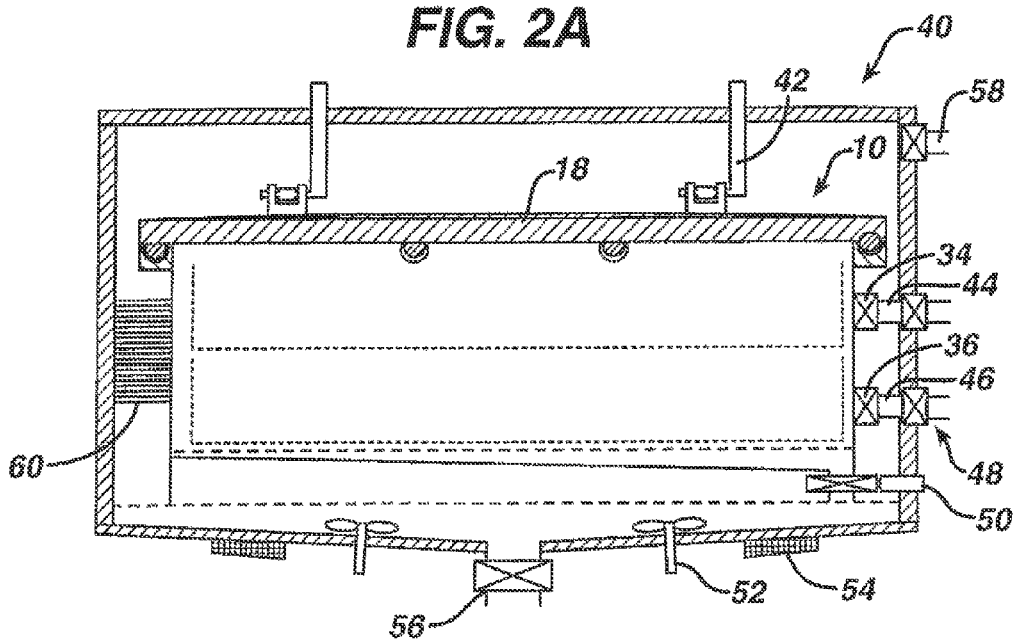
Figure 2B:
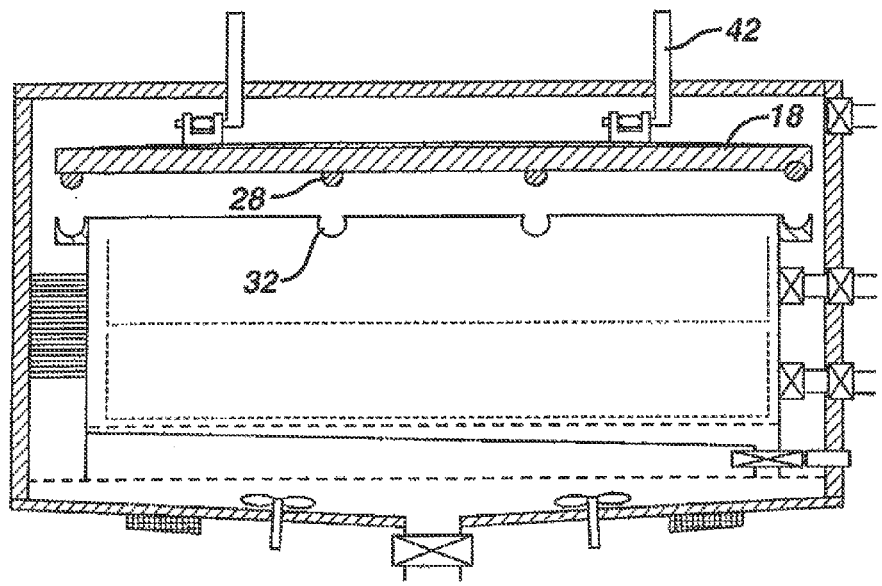

Turning now also to FIGS. 2a and 2b, the container 10 is shown within a chamber 40. A pair of lifting rods 42 are adapted to engage the brackets 38 and can be employed for automatically opening and closing the lid 18 while the container 10 is positioned within the chamber 40. Although a mechanical interaction is shown, other methods of engaging the lid could be employed such as an electromagnetic connection. First and second lines 44 and 46 connect to the first and second valved openings 34 and 36 respectively and can further include their own valves 48. A transducer 50 is provided for opening and closing the container drain valve 22. It can physically actuate the valve 22 or, alternatively, electrically or electromagnetically actuate the valve 22. Agitators 52 and ultrasound transducers 54 are provided for exciting the washing fluid within the container 10 to enhance cleaning ethicacy. The chamber 40 itself has several openings including a valved drain 56 and an inlet 58. Spacers and guides 60 are provided for providing proper positioning of the container 10 within the chamber 40.

Figure 3:
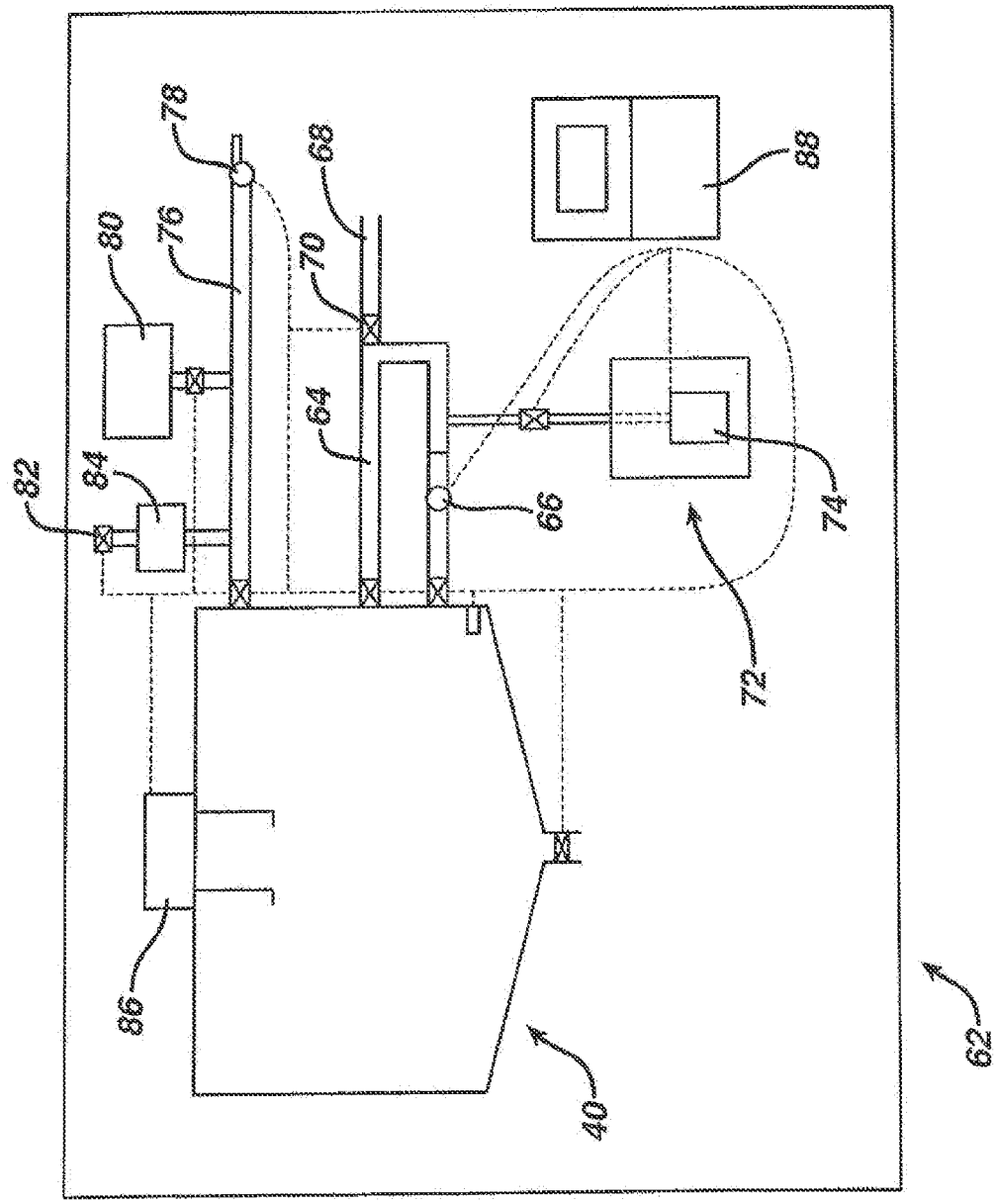

Turning now also to FIG. 3, the chamber 40 is shown within an integrated sterilization washing system 62. A circulation line 64 connects to first and second lines 44 and 46 respectively and has a recirculation pump 66. City water can enter through line 68 under control of a valve 70. Alternatively, fluid can flow into the container and chamber from both fluid lines 44 and 46, and flow out from drains 20 and 58. A cleaning fluid injection system 72 meters and delivers cleaning fluid from a reservoir 74. One preferable cleaning solution is ENZOL enzymatic cleaning solution available from Advanced Sterilization Products Division of Ethicon, Inc. in Irvine, Calif. Line 76 connects to the chamber inlet 58 and also to a vacuum pump 78, a germicide injection system 80 and a vent 82 with a filter 84 for allowing sterile filtered air to enter the chamber 40. An actuator 86 is provided for operating the lifting rods 42. A control system 88 controls the devices within the system 62, provides feedback to a user and allows entry of information about the instruments to be cleaned from a user.

The cleaning and sterilization starts with placing contaminated devices in a container. Preferably, this occurs at the point of use, such as in an operating room. The container may be filled with soaking fluid to prevent contaminates on the devices from drying and becoming more difficult to remove. The soaking fluid may comprise a liquid solution of cleaning and/or sterilization chemicals, or more preferably a foam of comprising an enzymatic cleaner or hydrogen peroxide. After the container is sealed, the contaminants and pathogens are sealed inside and the container may be transported by personnel not wearing protective gloves, garments etc.

The container is then inserted into the chamber 40 and the chamber 40 is sealed. The chamber 40 may be heated to enhance the cleaning and sterilization process. Preferably, the chamber is heated to 30° C. to 60° C. The lifting rods 42 lift the lid 18. The soaking fluid may be used for further cleaning or drained. Preferably, it is drained and rinsed by opening the drain 22 and flowing water in through the opening 34. The drain 22 is then closed and the container 10 is filled with a cleaning solution comprising water and concentrated cleaning fluid from the reservoir 74. This is re-circulated by the pump 66. If the additional agitation of the agitators 52 and ultrasound transducers 54 is required then the drain 22 is left open and the chamber 40 also filled with cleaning solution. By separating the lid from container, it exposes one most likely contaminated area between the lid 18 and container 10 for cleaning and sterilization. Rinsing fluid is then used to remove the cleaning chemicals. The rinsing fluid may be city water, DI water or distilled water.

Next, germicide is admitted to the chamber 40. The germicide may be introduced as liquid, mist, vapor, or gas to treat the devices, container and chamber. The germicide may comprise hydrogen peroxide, peracetic acid, performic acid, or ozone. The sterilization process may be hydrogen peroxide vapor from pre-treated liquid peroxide or solid peroxide complex. It may be steam or ethylene oxide. Preferably, the sterilization process comprises admitting heated air through inlet 58 to dry the chamber 40 and its contents followed by sealing the chamber and lowering the pressure via the vacuum pump 78 to below 1 torr whereupon a 59% hydrogen peroxide solution is vaporized into the chamber 40 and left in contact with for a sufficient period of time to effect sterilization of the container 10 and the instruments 12 therein. After the sterilization is completed, the lid 18 and drain 20 are all closed and the container is ready to be removed from the chamber 40. The sterility of the instruments 12 is maintained by the sealed container 10.

Figure 4A:
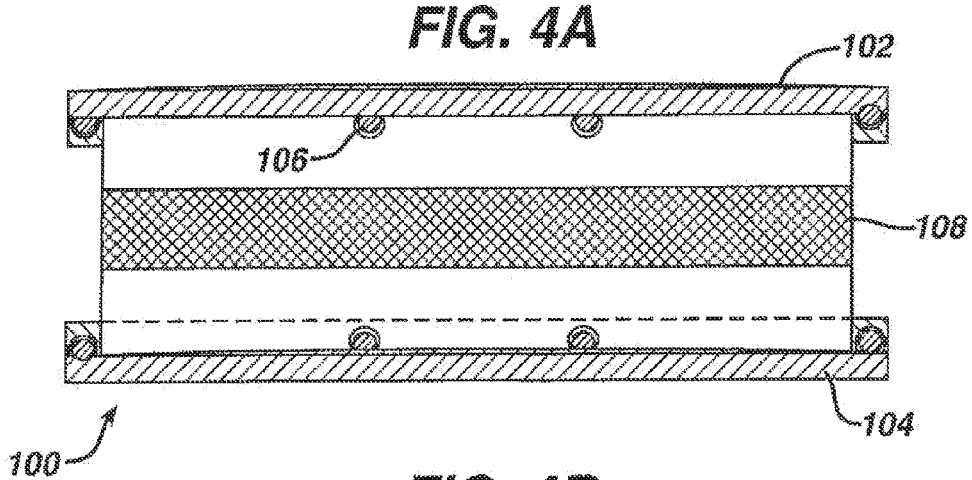
FIG. 4a is a side elevation view of an alternative container according to the present invention.
Figure 4B:
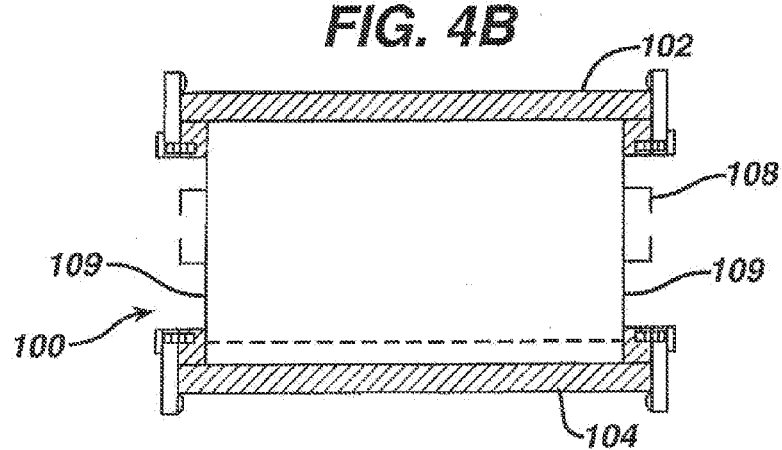
Figure 4C:
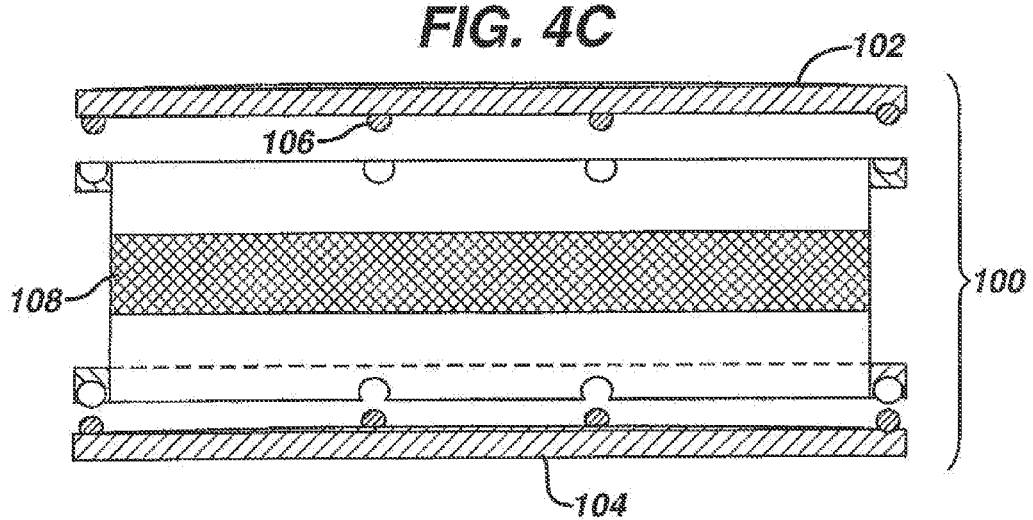
FIG. 4c is a side elevation view of the container of FIG. 4a, shown with its top and bottom removed.
Figure 5A:
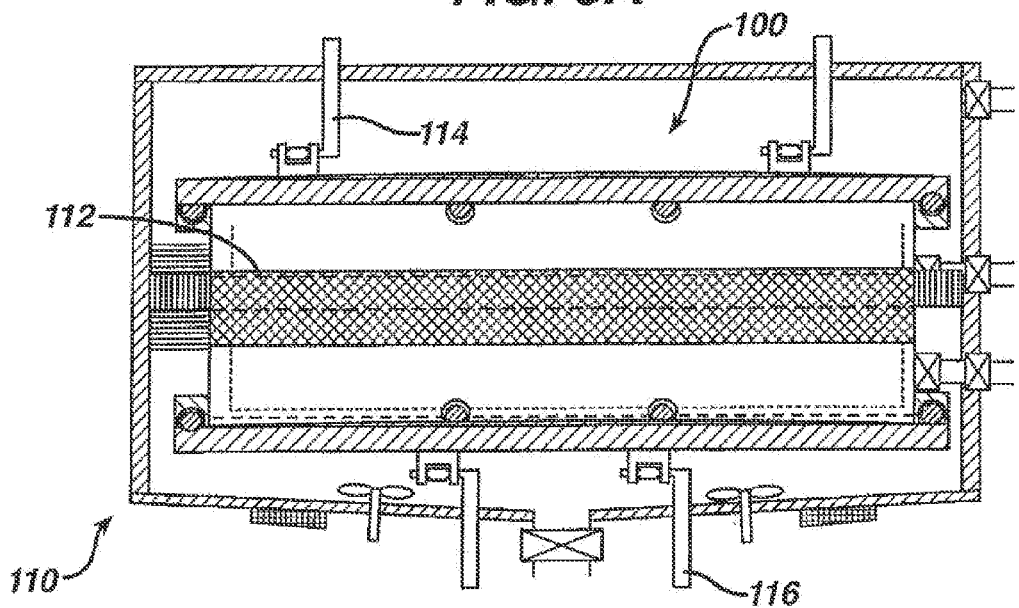
Figure 5B:
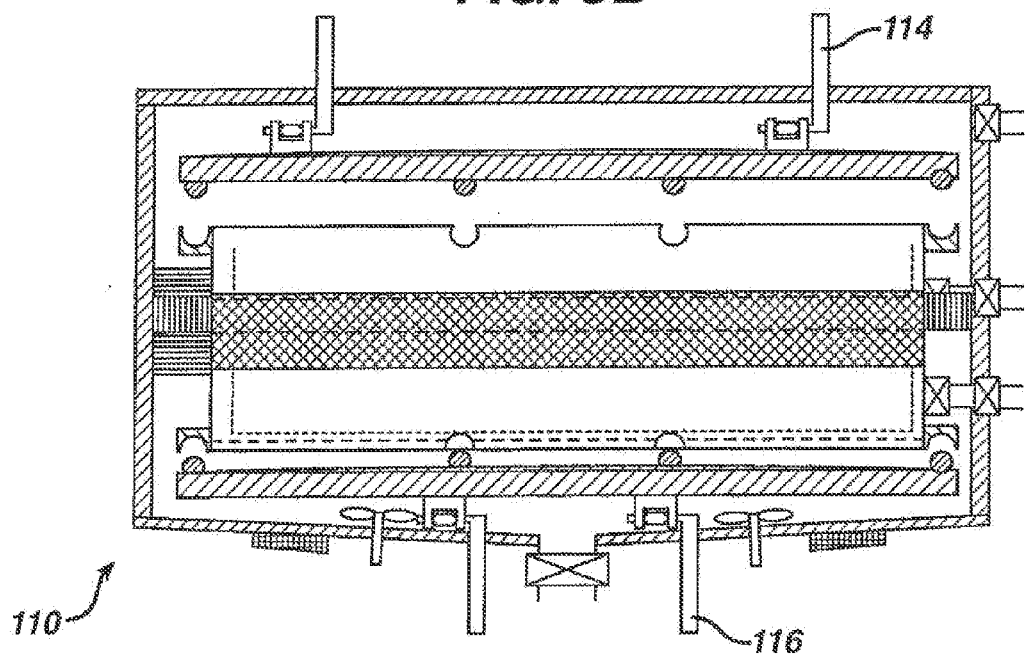

FIGS. 4a, 4b and 4c show an alternative container 100. It comprises a removable lid 102 and removable bottom 104 each with locating bosses 106 as in the previous container. Flanges 108 are provided on two opposing sidewalls 109. Turning also now to FIGS. 5a and 5b, the container 100 is disposed within a chamber 110 similar to the previous chamber 40. Retaining members 112 fit within the flanges 108 to position the container 100 within the chamber 110. Upper lifting rods 114 and lower lifting rods 116 are provided for controlling opening and closing of the top 102 and bottom 104. In all other respects the container 100 and chamber 110 operate as in the previous embodiment with the added advantage of the bottom 104 being able to be removed during the process to enhance access of the cleaning fluid to the instruments during the cleaning procedure.

Figure 6A:
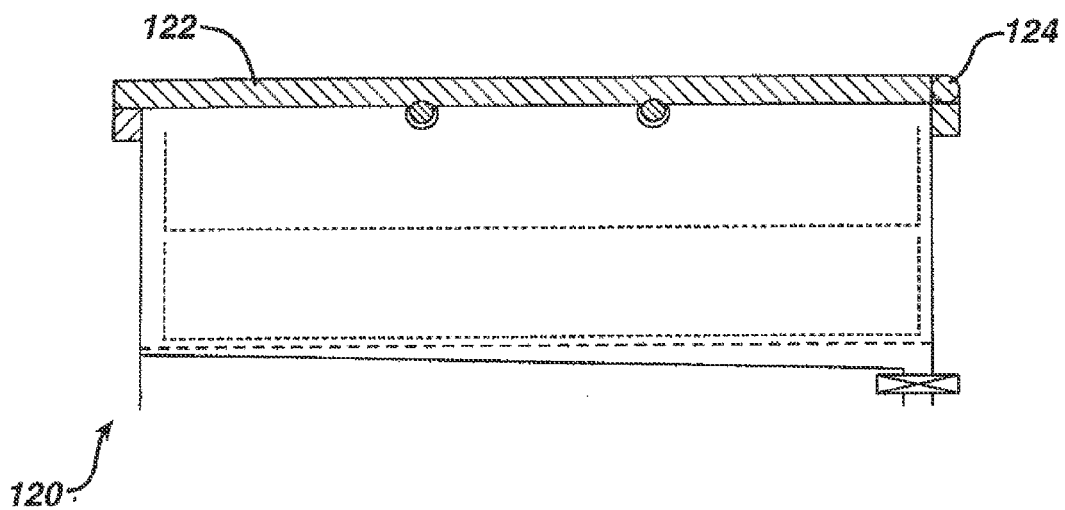
FIGS. 6a and 6b are side elevation views of a container according to the present invention.
Figure 6B:
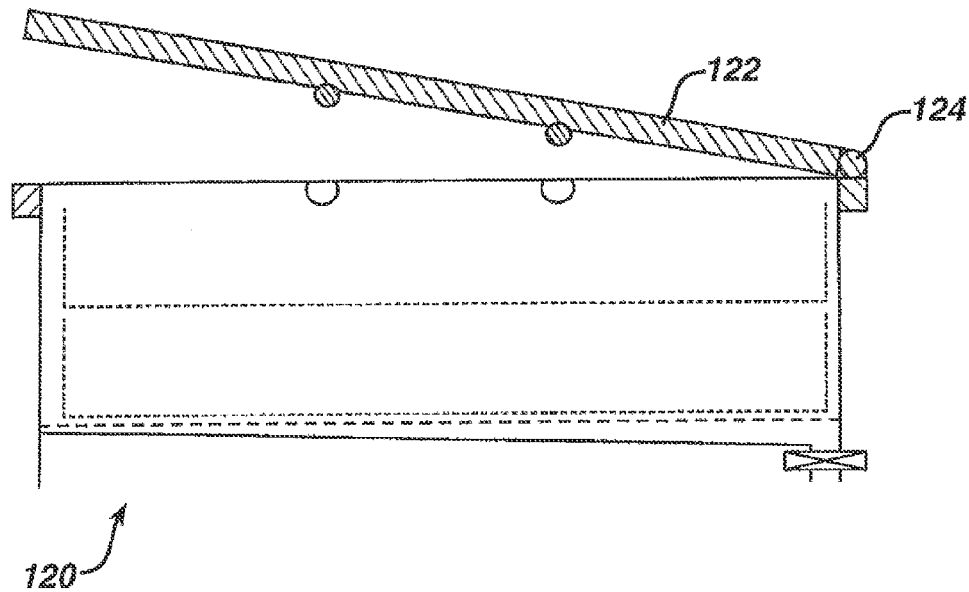

FIGS. 6a and 6b show an alternate version of a container 120. It has a lid 122 which attaches to the container 120 via a hinge 124. The hinge 124 helps ensure that the lid 122 will be properly positioned upon the container 120 when it is pushed into the closed position.

Figure 7A:
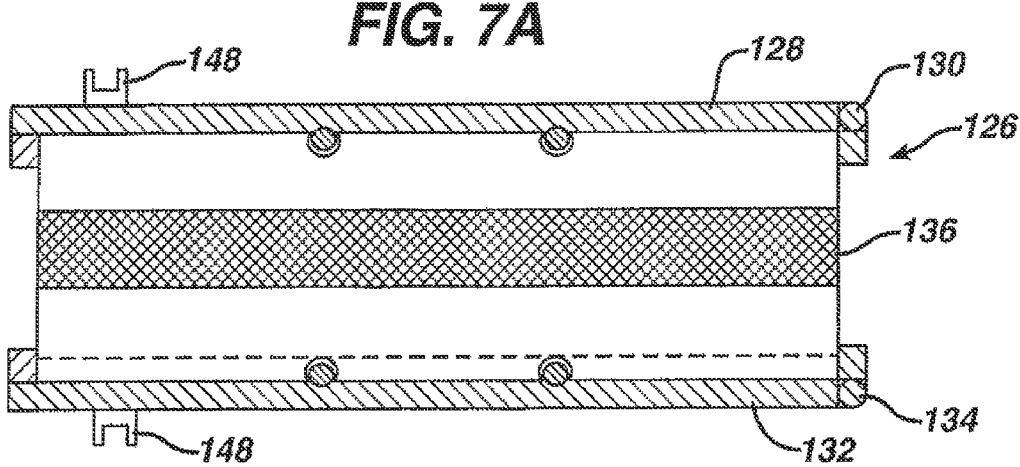
FIGS. 7a and 7b are side elevation views of a container according to the present invention.
Figure 7B:
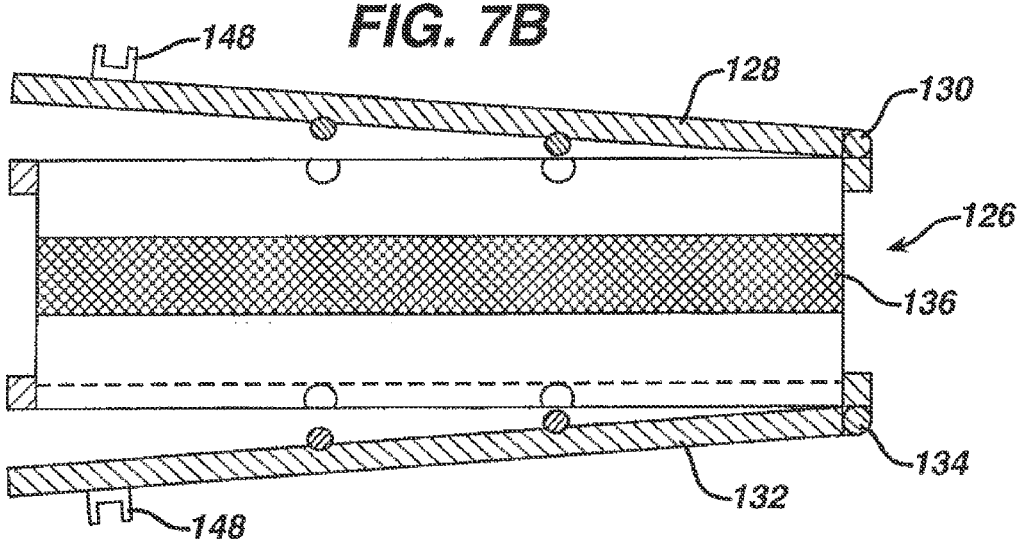
Figure 7C:
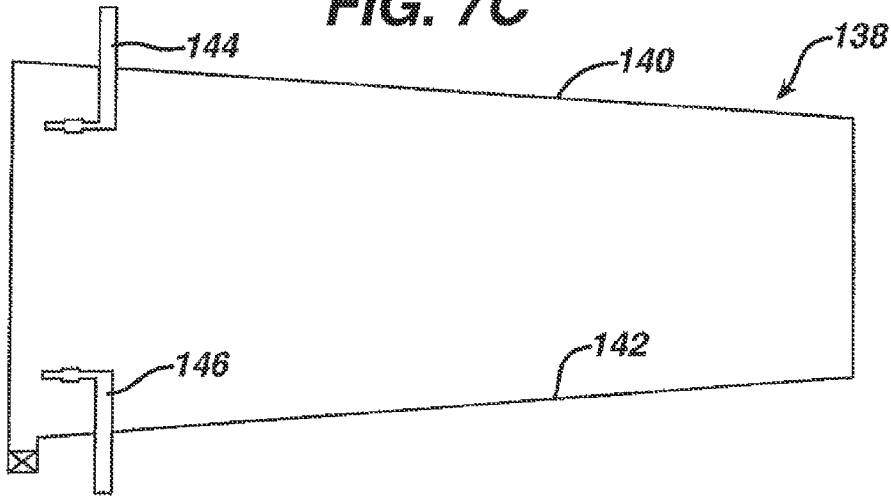

FIGS. 7a, 7b and 7c show a container 126 having a lid 128 attached via a hinge 130 and a bottom 132 attached via a hinge 134. Flanges 136 along its side portions function to hold the container similar to the flanges 108 of the container 100 of FIG. 4. A chamber 138 for receiving the container 126 as sloping upper and lower surfaces 140 and 142 to accommodate a container 126 with its lid 128 and bottom 132 opened. Upper and lower lifting rods 144 and 146 are provided for engaging brackets 148 on the lid 128 and bottom 132.

Figure 8A:
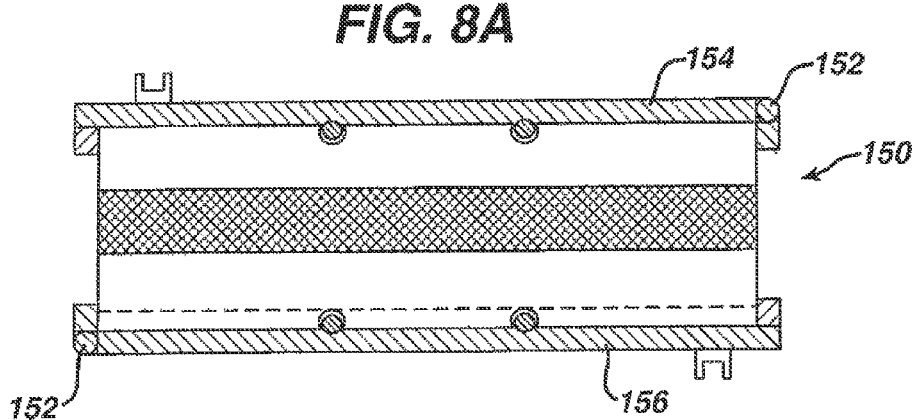
FIG. 8a is a side elevation view of a container according to the present invention.
Figure 8B:
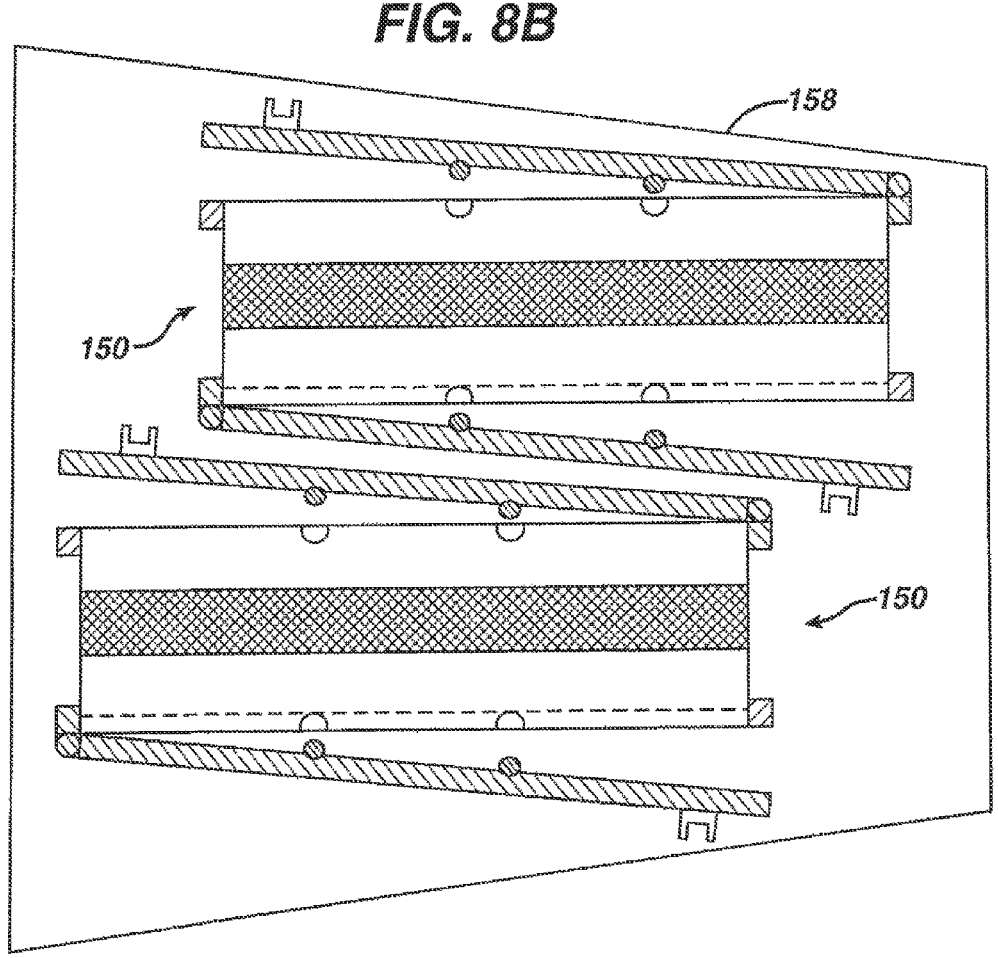

FIG. 8 shows a container 150 similar to the container 126 with the exception that it has hinges 152 for its lid 154 and bottom 156 on opposite side, thus allowing an alternate packing arrangement within a chamber 158.

Figure 9:
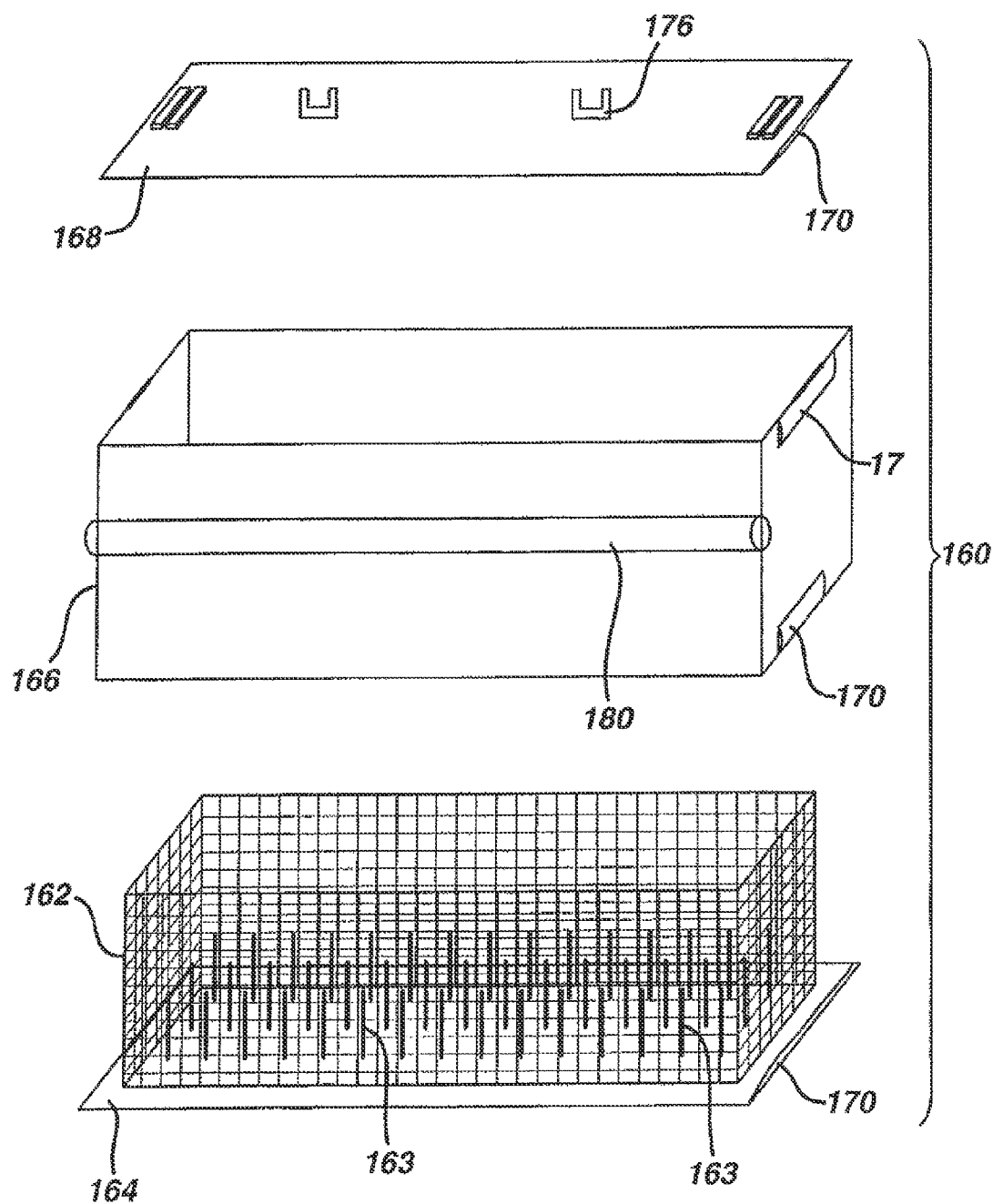
FIG. 9 is an exploded perspective view of a container according to the present invention.

FIG. 9 shows an alternative version of a container 160 comprising an inner basket 162, having upwardly extending silicone fingers 163 to limit shifting of items within the basket 162. The basket 162 rests on a bottom 164, which can either be removable or attached to the basket 162. Sidewalls 166 and a lid 168 are also removable. Spring loaded latches 170 hold the lid 168 to the sidewalls 166 and the sidewalls 166 to the bottom 164.

Figure 10A:
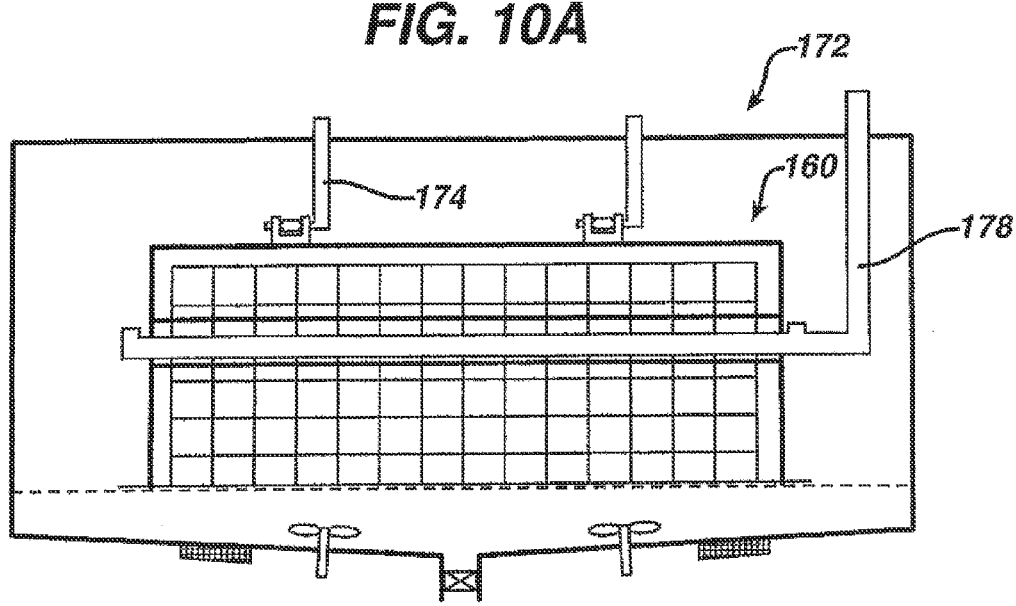
FIGS. 10a and 10b is a cut away side elevation view of a chamber according to the present invention receiving the container of FIG. 9.
Figure 10B:
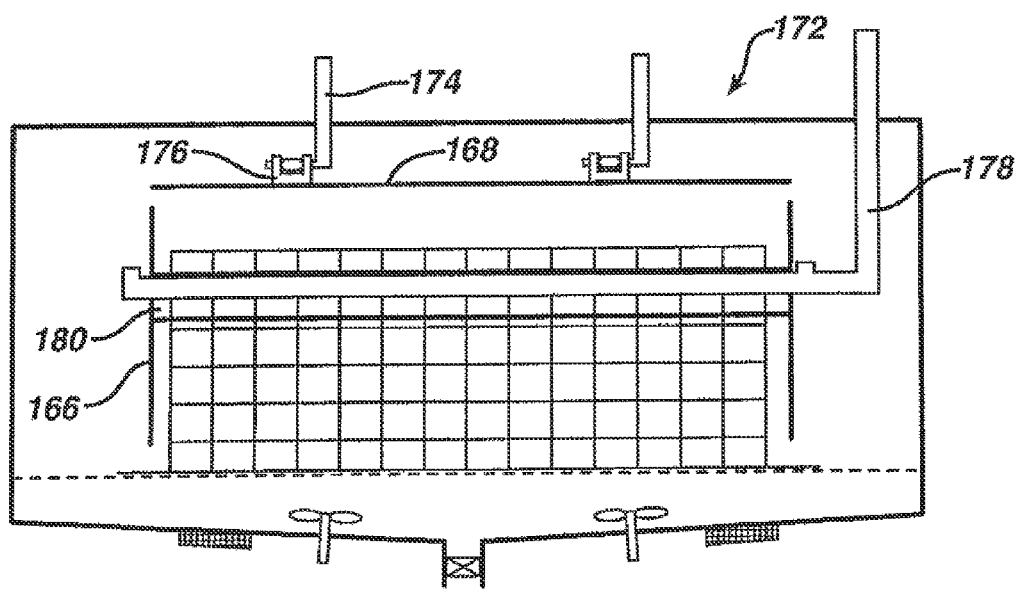

Turning also to FIGS. 10a and 10b, the container 160 is shown within a chamber 172. Lid lifting arms 174 engage brackets 176 on the lid 168 and side lifting arms 178 engage flanges 180 on the sidewalls 166 and their upward force disengages the latches 170 and exposes the basket 162 for better access of the washing fluid. When the sidewalls 166 and lid 168 are lowered the latches 170 automatically engage and seal the container 160.

FIG. 11 shows in an alternative arrangement in which an integrated washer and sterilizer 182 is separated into a separate washing section 184 and sterilization section 186 separated by a movable partition 188. It employs a container 190 having an internal basket 192 on a bottom 194 and a removable cover 196 comprising sidewalls 198 and a top 200. Brackets 202 on the top 200 allow lifting arms 204 to place the cover 196 onto the bottom 194 and seal the container 190. Washing and rinsing occur in the washing section 184 where cleaning fluid is sprayed through nozzles 206 onto items in the basket 192. Ultrasound transducers and agitators (not shown in FIG. 11) as in previous embodiments may be employed in place of or in addition to the nozzles 206.

After the washing cycle the partition 188 is opened, the basket 192 is pushed via an actuator 208 into the sterilization section 186 and the partition 188 closed. In the sterilization section 186 a sterilization process employing steam or vapor phase chemical sterilization is carried out. Preferably, it involves a vapor phase hydrogen peroxide process via vaporizing a liquid peroxide solution or releasing hydrogen peroxide from a solid peroxide complex as previously described. After the process is complete the cover 196 is lowered onto the bottom 194 to seal the container 190 and maintain the sterility of the instruments therein.

Optionally, semi-permeable filters 210 can be provided on the container 190 to allow a vapor phase sterilization process to be carried out with the cover 196 sealed to the bottom 194. Further, the container 190 having a cover 196 which leaves the basket 192 open during both cleaning and sterilization can be employed with any of the previously described chambers.

Figure 12:
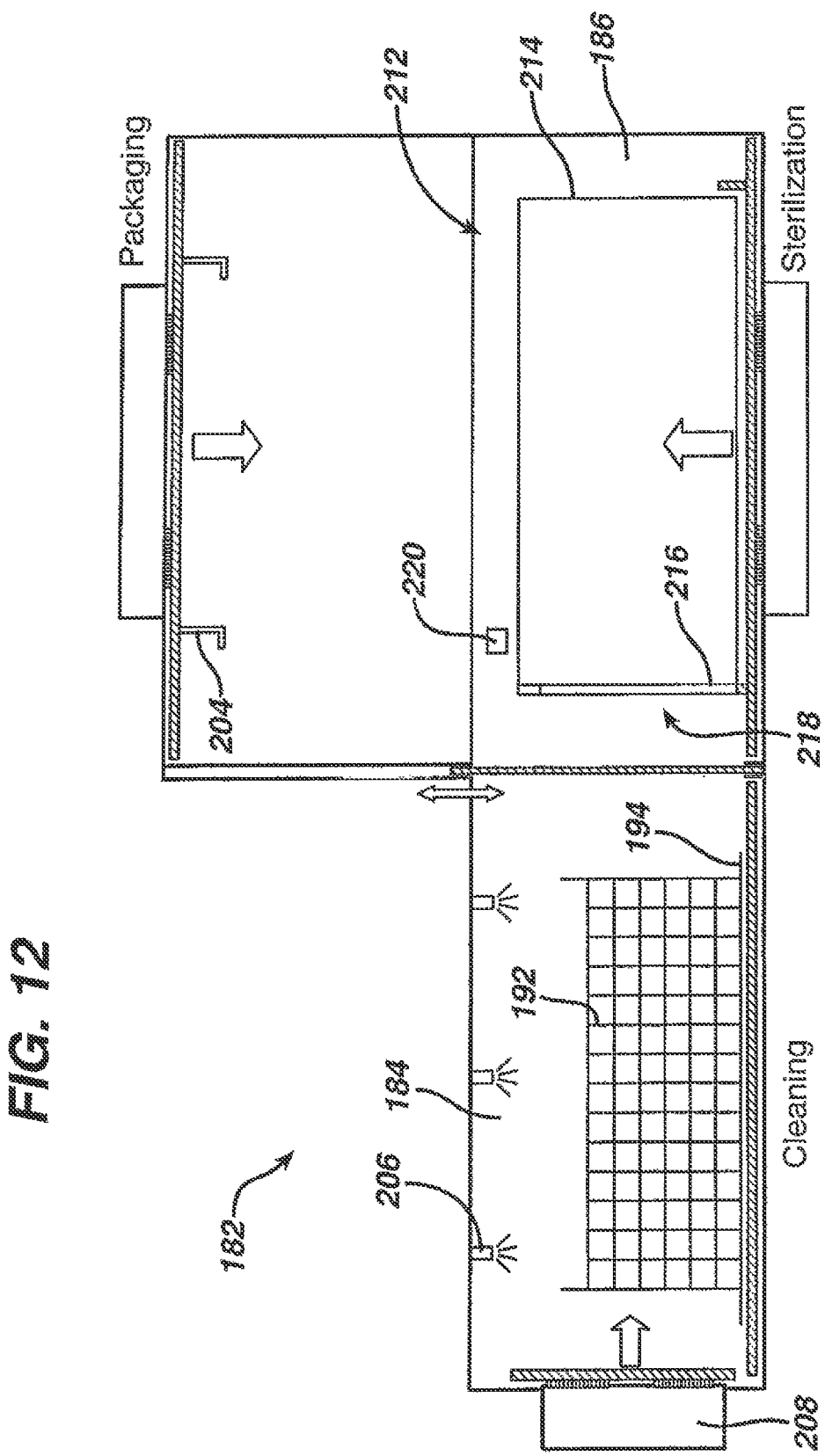
FIG. 12 is a cut away side elevation view of the washer/sterilizer of FIG. 11 showing a packaging apparatus.

FIG. 12 shows the integrated washer/sterilizer 182 with an automated packaging apparatus 212. A pouch 214 is preloaded onto a collapsible frame 216 with an open end 218 facing the washing section 184. The pouch is made of a semi-permeable material permeable to sterilizing gasses and impermeable to sterilant vapors. Suitable materials include TYVEK (spunbonded olefin) or SMS (spunbond polypropylene, melt blown polypropylene, spunbond polypropylene). As the basket 192 or tray is pushed into the sterilizing section 186 it enters the pouch 214 which is then sealed closed with a heat sealing iron 220 which lowers to compress and seal the pouch 214 at the opening 218, or alternatively sealed via adhesive at the opening 218. After the instruments are sealed within the pouch 214 the sterilization cycle occurs.

With separated washing 184 and sterilization sections 186, the system 182 can be operated as a washer and a sterilizer simultaneously, or an integrated washer/sterilizer and can be adapted to many cleaning, disinfecting and sterilization techniques. The packaging may be performed between cleaning and sterilization or after sterilization. Optionally, the packaging area and sterilization area can be separated with a removable divider. If packaging is not required, then the sterilization process may only occur in the sterilization area. Optionally, the packaging area may be located on the same level as the cleaning area and sterilization area. The packaging area may be located between cleaning area and sterilization area, or after the sterilization area. The packaging can be performed with container, pouch or wrap. The following examples represent a few of the many possible processes.

Example A

Step 1: Loading a load in wire basket or tray into the right-most cleaning area

Step 2: Cleaning the load in the cleaning area. Optionally, this step may include detergent, surfactant, enzyme, cleaning chemical, spray, agitation, or ultrasound.

Step 3: Rinsing the load with water. Preferably, the water is distilled water, or DI water.

Step 4: Treating load with liquid hydrogen peroxide. Preferably, the liquid is in the form of mist.

Step 5: Moving load into the middle packaging area.

Step 6: Sliding load into an open gas permeable pouch and sealing the pouch. Optionally, the packaging may be a container with gas permeable barrier or CSR wrap.

Step 7: Moving load into the right-most sterilization area

Step 8: Reducing the pressure to below the vapor pressure of hydrogen peroxide.

Step 9: Sterilizing the load with vaporized peroxide. Optionally, the process further comprises exciting the atmosphere into plasma to complete the process.

Example B

Step 1: Loading a load in wire basket or tray into the right-most cleaning area.

Step 2: Cleaning the load in the cleaning area. Optionally, this step may include detergent, surfactant, enzyme, cleaning chemical, spray, agitation, or ultrasound.

Step 3: Rinsing the load with water. Preferably, the water is distilled water, or DI water.

Step 4: Moving the load into the middle packaging area.

Step 5: Sliding the load into an open gas permeable pouch and sealing the pouch. Optionally, the packaging may be a container with a gas permeable barrier or CSR wrap.

Step 6: Moving the load into the right-most sterilization area.

Step 7: Sterilizing the load.

Example C

Step 1: Loading a load in wire basket or tray into the cleaning area.

Step 2: Cleaning the load in the cleaning area. Optionally, this step may include detergent, surfactant, enzyme, cleaning chemical, spray, agitation, or ultrasound.

Step 3: Rinsing the load with water. Preferably, the water is distilled water, or DI water.

Step 4: Moving the load into the sterilization area.

Step 5: Sterilizing the load.

Step 6: Moving the load into the packaging area.

Step 7: Packaging the load with sterile pouch, container or CSR wrap.

Example D

Step 1: Placing a load into a container with lid.

Step 2: Loading the container into the integrated washer/sterilizer 182. Optionally, the washer/sterilizer can be a washer/decontaminator or washer/disinfector.

Step 3; Opening the lid. Optionally, the bottom can be opened.

Step 4: Cleaning the load, container and lid. Optionally, this step may include detergent, surfactant, enzyme, cleaning chemical, spray, agitation, or ultrasound.

Step 5: Rinsing the load, container, and lid with water. Preferably, the water is distilled water, or DI water.

Step 6: Sterilizing the load, container and lid.

Step 7: Closing the container.

Example E

Step 1: Placing a load into a container with lid.

Step 2: Soaking the load with soaking fluid. Optionally, the soaking fluid may include detergent, surfactant, enzyme, or peroxide. The soaking fluid may be liquid or foam. Optionally, the container has a soaking indicator to indicate the proper soaking of load (both the soaking fluid is deep enough to cover the instruments and that the time period is sufficient).

Step 3: Loading the container into the integrated washer/sterilizer. Optionally, the washer/sterilizer can be a washer/decontaminator or washer/disinfector.

Step 4; Opening the lid. Optionally, the bottom can be opened.

Step 5: If necessary, further cleaning the load, container and lid. Optionally, this step may include detergent, surfactant, enzyme, cleaning chemical, spray, agitation, ultrasound, or defoaming agent.

Step 6: Rinsing the load, container, and lid with water. Preferably, the water is distilled water, or DI water.

Step 7: If necessary, further decontaminating, disinfecting, or sterilizing the load, container and lid.

Step 8: If necessary closing the container.

A simple use for the containers, such as the container 10, and systems and chambers, such as chamber 40 as shown in FIGS. 1a, 1b, 2a, 2b and 3, is to provide an automated washing and decontamination procedure which is sealed from human contact such that the personnel do not require elaborate protective garb. This process would be followed by a traditional packaging and sterilization. In such a process the instruments 12 are placed into the container 10 as their use is completed in a procedure. They are covered with a soaking fluid or foam and then the container is sealed. It can now be transported to and loaded into the chamber 40 by personnel who are not in full protective garb. In the chamber 40 the lid 18 is opened, the drain valve 22 is opened and the instruments are rinsed. The drain valve 22 is then closed and the container 10 is filled with a cleaning solution comprising water and concentrated cleaning fluid from the reservoir 74. This is re-circulated by the pump 66. If the additional agitation of the agitators 52 and ultrasound transducers 54 is required then the drain valve 22 is left open and the chamber 40 also filled with cleaning solution. By separating the lid from container, it exposes one most likely contaminated area between the lid 18 and container 10 for cleaning and decontamination. Rinsing fluid is then used to remove the cleaning chemicals. The rinsing fluid may be city water, DI water or distilled water. Then the instruments are decontaminated, i.e. disinfected sufficiently so as to allow safe inspection and handling of the instruments. Preferably, this would be a flash cycle comprising pumping down the chamber to below 1 torr, vaporizing 59% percent hydrogen peroxide into the chamber and contacting the instruments for five minutes. Alternatives include a short steam cycle, or immersion in a liquid peroxide solution, or other liquid sterilants such as orthophthalaladehyde, followed with a rinse. The instruments 12 are now safe for inspection, handling and packaging for sterilization. Replacing the lid 18 automatically is optional, although probably the most convenient for the operating personnel.

While the invention has been particularly described in connection with specific embodiments thereof, it is to be understood that this is by way of illustration and not of limitation, and that the scope of the appended claims should be construed as broadly as the prior art will permit.

What is claimed is:

1. An apparatus for cleaning and decontaminating one or more medical instruments sealed within a container, the apparatus comprising: a chamber for receiving the container; opening means comprising one or more arms attached to a lid of the container and an actuator for causing the one or more arms to lift the lid off of the container, for opening the container automatically while it is inside the chamber; a washing fluid distribution system connected to the chamber whereby to apply washing fluid to the device within the chamber; and a source of decontamination fluid connected to the chamber whereby to decontaminate the instruments after washing.

2. An apparatus according to claim 1 wherein the decontamination fluid comprises hydrogen peroxide vapor.

3. An apparatus according to claim 1 and further comprising a computer control system connected to the opening means, the washing fluid distribution system and the source of decontamination fluid and wherein the computer is programmed to, after the chamber is sealed, open the container via the opening means, wash the device via the washing fluid distribution system and decontaminate the device via the decontamination fluid.

4. An apparatus according to claim 1 wherein the container comprises an internal basket and removable sides and top whereby to expose the basket for efficient washing.

5. An apparatus according to claim 4 wherein the basket further comprises a plurality of upwardly extending resilient fingers therein whereby to limit movement of the instruments within the basket.

* * * * *